United States Patent [19]

Peet et al.

[11] Patent Number: 5,011,835
[45] Date of Patent: Apr. 30, 1991

[54] SUBSTITUTED TRIAZOLOPYRIDAZINES, PHARMACEUTICAL COMPOSITIONS AND USE

[75] Inventors: Norton P. Peet, Cincinnati, Ohio; Shyam Sunder, Indianapolis, Ind.

[73] Assignee: Merrell Dow Pharmaceuticals Inc., Cincinnati, Ohio

[21] Appl. No.: 476,195

[22] Filed: Feb. 7, 1990

[51] Int. Cl.$^5$ ..................... A61K 31/50; A61K 31/55; C07D 487/04
[52] U.S. Cl. ................................. 514/212; 514/233.2; 514/248; 540/599; 544/118; 544/234; 424/45
[58] Field of Search ................ 540/599; 544/118, 234; 424/45; 514/212, 233.2, 248

[56] References Cited

U.S. PATENT DOCUMENTS 4,526,890  7/1985  Peet et al. .......................... 544/234

Primary Examiner—Robert W. Ramsuer
Attorney, Agent, or Firm—John J. Kolano

[57] ABSTRACT

This invention is directed to a group of compounds which are acyl derivatives of amino substituted triazolopyridazines. They are prepared by the reaction of an aminotriazolopyridazine or an aminotriazolophthalazine with an appropriate acid chloride. These compounds possess bronchodilating and antiallergenic activity.

19 Claims, No Drawings

SUBSTITUTED TRIAZOLOPYRIDAZINES, PHARMACEUTICAL COMPOSITIONS AND USE

The present invention is directed to a group of compounds which are acyl derivatives of amino substituted triazolopyridazines. These compounds have the following general formula:

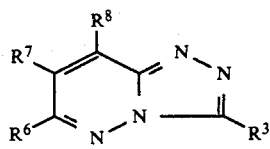

wherein $R^6$ is

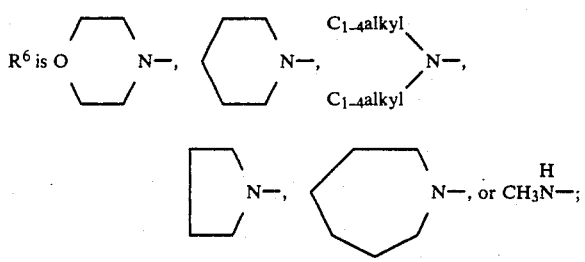

$R^7$ and $R^8$ are each independently H or $CH_3$, or $R^7$ and $R^8$ together are $-CH_2CH_2CH_2CH_2-$; and when $R^7$ and $R^8$ are together $-CH_2CH_2CH_2CH_2-$, then,

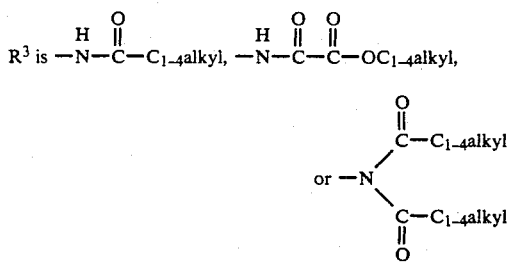

and when $R^7$ and $R^8$ are each independently H or $CH_3$, then

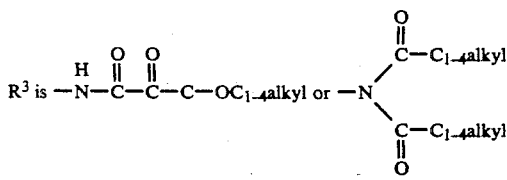

Examples of $C_{1-4}$ alkyl in $R^3$ and $R^6$ include methyl, ethyl, propyl, isopropyl, butyl, isobutyl, sec-butyl, sec-butyl, and tert-butyl.

The acid addition salts of the above compounds with pharmaceutically acceptable acids are considered equivalent to the above identified compounds for purposed of this invention. Illustrative of these salts are the salts formed with inorganic acids, for example, hydrochloric, hydrobromic, sulfuric, phosphoric, and like acids; with organic carboxylic acids, for example, acetic, propionic, glycolic, lactic, pyruvic, malonic, succinic, fumaric, malic, tartaric, citric, ascorbic, maleic, hydroxymaleic and dihydroxymaleic, benzoic, phenylacetic, 4-aminobenzoic, 4-hydroxybenzoic, anthranilic, cinnamic, salicylic, 4-aminosalicylic, 2-phenoxybenzoic, 2-acetoxy-benzoic, mandelic, and like acids; and with organic sulfonicacids, for example, methanesulfonic acid and p-toluenesulfonic acid.

The compounds of the present invention possess bronchodilating and antiallergic activity. Thus, they are useful in the treatment of bronchial disorders, for example, bronchial asthma, and in the treatment of conditions in which antigen-antibody reactions are responsible for disease and particularly in the treatment of allergic conditions, diseases, or reactions, for example, extrinsic asthma, hay fever, urticaria, eczema or atopic dermatitis, and upper respiratory conditions such as allergic rhinitis. The present invention is further directed to a method of effecting bronchodilation.

The compounds of the present invention may be administered either as individual therapeutic agents or as mixtures with other therapeutic agents. They may be administered alone, but are generally administered in the form of pharmaceutical compositions, i.e., mixtures of the active compound with suitable pharmaceutical carriers or diluents. Examples of such compositions include tablets, lozenges, capsules, powders, aerosol sprays, aqueous or oily suspensions, syrups, elixirs, and aqueous solutions for injection.

Suitable pharmaceutical carriers and formulation techniques may be found in standard texts such as *Remington's Pharmaceutical Sciences*, 15th Edition, Mack Publishing Company, Easton, Penna. For example, oral compositions may be in the form of tablets or capsules and may contain conventional excipients such as: binding agents, for example, syrup, acacia, gelatin, sorbitol, tragacanth, or polyvinylpyrrolidone; fillers, for example, lactose, sugar, maize-starch, calcium phophate, sorbitol, or glycine; lubricants, for example, magnesium stearate, talc, polyethylene glycol, or silica; disintegrants, for example, starch; or wetting agents, for example, sodium lauryl sulfate. Oral liquid preparations may be in the form of aqueous or oily suspensions, solutions, emulsions, syrups, elixirs, etc., or may be presented as a dry product for reconstitution with water or other suitable vehicle before use. Such liquid preparations may contain additional additives such as suspending agents, flavoring agents, diluents, or emulsifying agents. For parenteral administration or inhalation, solutions or suspensions of a compound of the present invention with conventional pharmaceutical vehicles may be employed such as, for example, an aerosol spray for inhalation, an aqueous solution for intravenous or intraperitoneal injection, or an oily suspension for intramuscular injection. The compounds may also be administered by means of inhalers or other devices which permit the active compounds in the form of a spray, aerosol, or dry powder to come into direct contact with the lungs.

In practicing the method of this invention for producing bronchodilation or an antiallergenic effect, a pharmaceutically effective amount of one or more of the substituted triazolopyridazines of the present invention is preferably administered in the form of a pharmaceutical composition to a patient in need thereof. The nature of the pharmaceutical composition will, of course, depend on the desired route of administration, i.e., oral, parenteral, or inhalation.

As used herein, the term "patient" refers to a warm-blooded animal, such as a mammal. It is understood that dogs, cats, rats, mice, horses, cattle, sheep, and humans are examples within the scope of the meaning of the term.

The pharmaceutically effective amount of the compound for producing bronchodilation or an antiallergenic effect depends on various factors. These factors include, for example, the size, type, and age of the patient to be treated, the particular compound employed, the route and frequency of administration, the severity of symptoms and causative agent involved, and the time of administration. In particular cases, the dosage to be administered can be ascertained by conventional dosage range finding techniques, for example, by observing the bronchodilating and/or antiallergic activity produced at different dosage rates. More specifically, these compounds may be administered at dosages ranging from about 0.1 to 250 mg. per kg. of patient body weight. It is generally desirable to administer individual dosages at the lowest amount providing the desired response, consonant with a convenient dosing schedule.

In evaluating bronchodilator activity, test compounds were administered to male Hartley-Duncan guinea pigs by intraperitoneal injection. The guinea pigs were then challenged by exposure to a histamine aerosol at periods ranging from 15 minutes to 4 hours after injection of the test compound. The animals were observed and collapse times were recorded. Untreated animals collapsed when they were exposed to the histamine aerosol. When tested by this procedure, the compounds of the present invention were found to produce a bronchodilating effect.

The actual dose of test compound administered was generally 30% of the $LD_{50}$ administered intraperitoneally. Some specific doses of compounds used in the above testing were:

((6-(1-Piperidinyl)-1,2,4-triazolo[4,3-b]pyridazin-3-yl)amino)-oxoacetic acid ethyl ester: 31 mg/kg, ((6-(1-Piperidinyl)-1,2,4-triazolo[4,3-b]pyridazin-3-yl)amino) oxoacetic acid methyl ester: 113 mg/kg, 3-Amino-6-(methylamino)triazolo[4,3-b]pyridazine: 387 mg/kg, 3-Amino-6-(methylamino)-7,8,9,10-tetrahydro-1,2,4-triazolo-[3,4-a]phthalazine: 113 mg/kg, 3-Amino-6-(1-piperidinyl)-7,8,9,10-tetrahydro-1,2,4-triazolo[3,4-a]phthalazine: 74 mg/kg, N-(7,8,9,10-Tetrahydro-6-(piperidinyl)-1,2,4-triazolo-[3,4-a]phthalazin-3-yl)acetamide: 62 mg/kg, N-(7,8,9,10-Tetrahydro-6-(1-piperidinyl)-1, 2,4-triazolo-[3,4-a]phthalazin-3-yl)propanamide: 66 mg/kg, N-((7,8,9,10-Tetrahydro-6-(1-piperidinyl)-1,2,4-triazolo-[3,4-a]phthalazin-3-yl)amino)oxoacetic acid methyl ester: 46 mg/kg, N-((7,8,9,10-Tetrahydro-6-(1-piperidinyl)-1,2,4-triazolo-[3,4-a] phthalazin-3-yl)amino)oxoacetic acid ethyl ester: 46 mg/kg, N-(7,8,9,10-Tetrahydro-6-(4-morpholinyl)-1, 2,4-triazolo-[3,4-a]phthalazin-3-yl)acetamide: 190 mg/kg, N-(7,8,9,10-Tetrahydro-6-(4-morpholinyl)-1, 2,4-triazolo-[3,4-a]phthalazin-3-yl)propanamide: 221 mg/kg, N-((7,8,9,10-Tetrahydro-6-(4-morpholinyl)-1, 2,4-triazolo[3,4-a]-phthalazin-3-yl)-amino)oxoacetic acid ethyl ester: 190 mg/kg, 3-Amino-6-(4-morpholinyl)-7,8,9,10-tetrahydro-1, 2,4triazolo[3,4-a]phthalazine hydrochloride: 190 mg/kg, 3-Amino-6-(1-pyrrolidinyl)-7,8,9,10-tetrahydro-1, 2,4triazolo[3,4-a]phthalazine: 116 mg/kg, and N-((7,8,9,10-Tetrahydro-6-(1-pyrrolidinyl)-1, 2,4-triazolo-[3,4-a]phthalazin-3-yl)amino)oxoacetic acid ethyl ester: 11 mg/kg.

The antiallergic activity of the present compounds is demonstrated by the IgE mediated Passive Cutaneous Anaphylaxis (PCA) test. This test is generally accepted as one of the best animal models for the qualitative determination of antiallergic activity. Disodium cromoglycate is active in this test when administered intraperitoneally, but not orally. The method can be described briefly as follows:

PCA Test Method

1. Antisera—Various standard methods described in the literature were used for the preparation of reaginic antisera to ovalbumin in either Hooded Lister or Brown Norway rats.
2. Animals—Adult male Sprague-Dawley or female Wistar Kyoto rats were used as antisera recipients in the test. The animals were allowed to acclimate for 5-14 days with food and water ad lib.
3. Sensitization—Recipient rats were passively sensitized by the intradermal injection of 100 microliters of two dilutions of antiserum (one injection on each side of the back). Sensitization occurred 48-72 hours prior to antigen challenge.
4. Administration of Test Compound—4 to 6 animals were used for each test compound/dilution. Compounds were homogenized in an appropriate carrier solution, and administered intraperitoneally at 60 mg/kg 5 minutes prior to challenge, or orally at 100 mg/kg 5 to 240 minutes prior to challenge.
5. Antigen Challenge and Reaction Evaluation—Ovalbumin (0.1-1.0 mg in a 0.5% solution of Evan's blue Dye) in saline was given to each rat by intravenous administration. Thirty minutes later, the resultant PCA reactions were measured for average diameter and color intensity from the reflected surface of the skin. Test compound activity is expressed as percent inhibition based on control reactions.

When tested by the above procedure, the compounds of the present invention were active both intraperitoneally and orally.

The compounds of the present invention are prepared by the following general procedure:

An amine of the formula

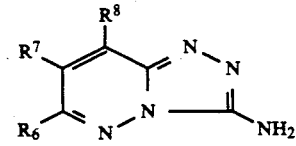

wherein $R^6$, $R^7$, and $R^8$ are defined as above, is reacted with an acid chloride of the formula

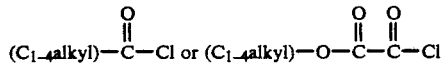

in an inert solvent with heating.

Specifically, these compounds may be prepared as follows:

A.

A hydrazino compound of the formula

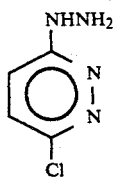

is taken up in methanol. To this mixture is added sodium acetate, then cyanogen bromide to form the chloro compound of the formula

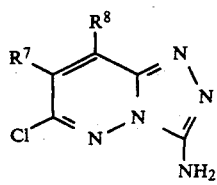

This compound is refluxed with the appropriate amine to form the amino compound of the formula

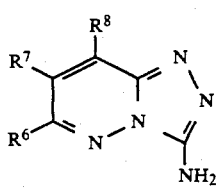

wherein $R^6$, $R^7$, and $R^8$ are defined as above.

To this compound is added the appropriate acid chloride to yield compounds comprising the present invention of the formula

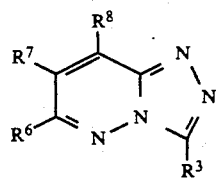

wherein $R^6$, $R^7$, and $R^8$ are defined as above, and $R_3$ is $-\overset{H}{N}-\overset{O}{\underset{\|}{C}}-C_{1-4}\text{alkyl}$, $-\overset{H}{N}-\overset{O}{\underset{\|}{C}}-\overset{O}{\underset{\|}{C}}-OC_{1-4}\text{alkyl}$, or $-N\begin{array}{c}\overset{O}{\underset{\|}{C}}-C_{1-4}\text{alkyl}\\ \overset{O}{\underset{\|}{C}}-C_{1-4}\text{alkyl}\end{array}$

B.

A hydrazino compound of the formula

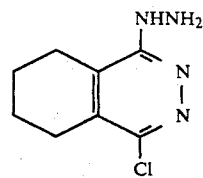

is taken up in methanol. To this mixture is added sodium acetate, then cyanogen bromide to form the chloro compound of the formula

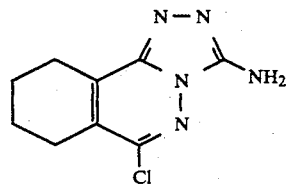

This compound is refluxed with the appropriate amine to form the amino compound of the formula

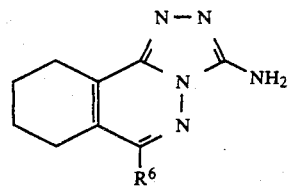

wherein $R^6$ is defined as above.

To this compound is added the appropriate acid chloride to yield compounds comprising the present invention of the formula

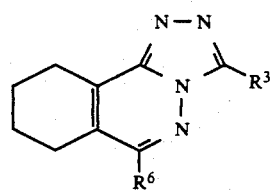

wherein $R^6$ and $R^3$ are defined as above.

Representative compounds of the present invention include, but are not limited to, the following:

((6-(1-Piperidinyl)-1,2,4-triazolo[4,3-b]pyridazin-3-yl) amino)oxoacetic acid ethyl ester, ((6-(1-Piperidinyl)-1,2,4-triazolo[4,3-b]pyridazin-3yl) amino)oxoacetic acid methyl ester, N-(7-Methyl-6-(1-piperidinyl)-1,2,4-triazolo [4,3-b]pyridazin-3-yl)propanamide N-(8-Methyl-6-(1-piperidinyl)-1,2,4-triazolo [4,3-b]pyridazin-3yl)propanamide 3-Amino-6-(methylamino)-7,8,9,10-tetrahydro-1,2,4-triazolo [3,4-a]phthalazine, 3-Amino-6-(1-piperidinyl)-7,8, 9,10-tetrahydro-1,2,4-triazolo[3,4-a]phthalazine, N-(7,8,9,10-Tetrahydro-6-(1-piperidinyl)-1, 2,4-triazolo-[3,4-a]phthalazin-3-yl)acetamide, N-(7,8,9,10-Tetrahydro-6-(1-piperidinyl)-1, 2,4-triazolo-[3,4-a]phthalazin-3-yl)propanamide, N-((7,8,9,10-Tetrahydro-6-(1-piperidinyl)-1,2,4-triazolo-[3,4-a]phthalazin-3-yl)amino)oxoacetic acid methyl ester, N-((7,8,9,10-Tetrahydro-6-(1-piperidinyl)-1,2,4-triazolo-[3,4-a]phthalazin-3-yl)amino)oxoacetic acid ethyl ester, N-(7,8,9,10-Tetrahydro-6-(1-piperidinyl)-1, 2,4-triazolo-[3,4-a]phthalazin-3-yl)-N-(propanoyl)propanamide, 3-Amino-6-(4-morpholinyl)-7,8,9,10-tetrahydro-1,2,4triazolo[3,4-a]phthalazine N-(7,8,9,10-Tetrahydro-6-(4-morpholinyl)-1,2,4-triazolo-[3,4-a]phthalazin-3-yl)acetamide, N-(7,8,9,10-Tetrahydro-6-(4-morpholinyl)-1,2,4-triazolo-[3,4a]phthalazin-3-yl)propanamide, N-((7,8,9,10-Tetrahydro-6-(4-morpholinyl)-1,2,4-triazolo[3,4-a]-phthalazin-3-yl)-amino)oxoacetic acid ethyl ester, 3-Amino-6-(4-morpholinyl)-7,8,9,10-tetrahydro-1,2,4triazolo[3,4-a]phthalazine hydrochloride, N-(1-Oxopropyl)-N-(7,8,9,10-tetrahydro-6-(4-morpholinyl)-1, 2,4triazolo-[3,4-a]phthalazin-3-yl)propanamide, 3-Amino-6-(1-pyrrolidinyl)-7,8,9,10-tetrahydro-1,2,4triazolo[3,4-a]phthalazine N-((7,8,9,10-Tetrahydro-6-(1-pyrrolidinyl)-1,2,4-triazolo-[3,4-a]phthalazin-3-yl)amino)oxoacetic acid ethyl ester.

The following examples are presented to illustrate the preparation of compounds comprising the present invention. They should not be construed as limiting it in any way.

EXAMPLE 1

3-Amino-6-chloro-1,2,4-triazolo[4,3-b]pyridazine

A 14.5 gm (0.100 mole) quantity of 3-chloro-6-hydrazino-pyridazine was added to 25 ml of methanol. To this mixture, 20.42 gm (0.150 mole) of sodium acetate was added and the mixture was stirred. While stirring, 10.60 gm of cyanogen bromide was added. The mixture became clear, followed immediately by the formation of a yellow precipitate, and the reaction was exothermic towards the end. The mixture was stirred for one hour at room temperature and filtered. The precipitate was washed with water and oven-dried to give 10.8 gm of 3-amino-6-chlorotriazolo[4,3-b]pyridazine; mp>300° C.

EXAMPLE 2

3Amino-6-(1-piperidinyl)-1,2,4-triazolo[4,3-b]pyridazine

A 5.0 gm (0.0295 mole) quantity of 3-amino-6-chlorotriazolo[4,3-b]pyridazine was refluxed overnight with 30 ml of piperidine. Some solid was still present. The mixture was evaporated, water was added to the residue, and 5.31 gm of solid 3-amino-6-(1-piperidinyl)-1,2,4-triazolo[4,3-b]pyridazine, mp 245-246° C., was collected.

EXAMPLE 3

((6-(1-Piperidinyl)-1,2,4-triazolo [4,3-b]pyridazin-3-yl)amino)oxoacetic acid ethyl ester A 6.00 gm (0.0275 mole) quantity of 3-amino-6-(1piperidinyl)triazolo[4,3-b]pyridazine was added to 300 ml of CH$_2$Cl$_2$. To this mixture, 11.33 gm (0.083 mole) of ethyl oxalyl chloride was added, and the resulting mixture was allowed to stand overnight. The mixture was worked up by extraction with water. The methylene chloride layer showed the presence of the starting material (5.4 gm) and a 3.5 gm quantity of ethyl oxalyl chloride was added to this solution. The mixture was stirred for 24 hours and it was then worked up by evaporating the organic layer and triturating with ether. A 4.95 gm quantity of solid ((6-(1-piperidinyl)-1,2,4-triazolo[4,3-b]-pyridazin-3-yl)amino)oxoacetic acid ethyl ester was collected; mp 188-189° C. (ethanol). Calculated: C, 52.82; H, 5.70; N, 26.40. Found: C, 52.62; H, 5.64; N, 26.02.

EXAMPLE 4

((6-(1-Piperidinyl)-1,2,4-triazolo[4,3-b]pyridazin-3-yl) amino)oxoacetic acid methyl ester A 6.00 gm (0.0275 mole) quantity of 3-amino-6-(1-piperidinyl) triazolo[4,3-b]pyridazine was added to 300 ml of toluene. To this mixture, 10.16 gm (0.083 mole) of methyl oxalyl chloride was added, resulting in a yellow solution. This mixture was allowed to stand overnight. The mixture was worked up by extraction with water. The organic layer was dried and evaporated and 6.16 gm of ((6-(1-piperidinyl)-1,2,4-triazolo [4,3-b]pyridazin-3-yl)amino)oxoacetic acid methyl ester, m.p. 184-185° C., was collected. Calculated: C, 51.31; H, 5.30; N, 27,62. Found: C, 51.20, H, 5.30, N, 27.5.

EXAMPLE 5

3-Amino-6-(4-morpholinyl)-1,2,4-triazolo[4,3-b]pyridazine

If the product of Example 1 is reacted with morpholine, the product obtained is 3-amino-6-(4-morpholinyl)-1,2,4triazolo[4,3-b]pyridazine.

EXAMPLE 6

3-Amino-6-(methylamino)triazolo[4,3-b]pyridazine

A 5.80 gm (0.0342 mole) quantity of 3-amino-6-chlorotriazolo[4,3-b]pyridazine was mixed with 25 ml of DMSO and warmed on a hot plate. The solid did not dissolve. A 200 ml volume of 40% aqueous methylamine was added and the mixture was heated in an oil bath at 80° C. for 24 hours. Most of the solid disappeared. An additional 50 ml of methylamine was added and the mixture was heated an additional 4 hours. The mixture became clear. The solution was partially concentrated and the resulting solid was filtered, washed with water, and dried. A 4.05 gm quantity of 3-amino-6-(methylamino)triazolo [4,3b]pyridazine, mp 292-294° C. was collected. Calculated: C, 43.89; H, 4.91; N, 51.20. Found: C, 43.84; H, 4.95; N, 51.45.

EXAMPLE 7

3-Amino-6-chloro-7,8,9,10-tetrahydro-1,2,4-triazolo[3,4-a]phthalazine

A 46.88 gm (0.236 mole) quantity of 1-chloro-4-hydrazino5,6,7,8-tetrahydrophthalazine was added to 450 ml of methanol. A 40.8 gm quantity of sodium acetate and 25.0 gm of cyanogen bromide was added and the mixture was stirred on a warm plate for 30 minutes. Yellow crystals appeared immediately. The mixture was allowed to sit for 3 days. The resulting solid was filtered, washed with ether, and dried, yielding 44.85 gm of 3-amino-6-chloro-7,8,9,10-tetrahydro-1,2,4-triazolo[3,4-a]phthalazine; mp 224-225° C. (ethanol).

EXAMPLE 8

3-Amino-6-(methylamino)-7,8,9,10-tetrahydro-1,2,4-triazolo[3,4-a]phthalazine

A 5.80 gm (0.0259 mole) quantity of the compound of Example 7 was taken up in 25 ml of DMSO and heated. To the warm mixture was added 250 ml of 40% aqueous methylamine. The resulting mixture was heated at 80° C. for 7 hours. The resulting mixture was evaporated to yield 3.66 gm of 3-amino-6-(methylamino)-7,8,9,10-tetrahydro-1, 2,4-triazolo[3,4-a]phthalazine; mp 295-297° C. Calculated: C, 55.03; H, 6.47; N, 38.51. Found: C, 54.79; H, 6.42; N, 38.60.

EXAMPLE 9

3-Amino-6-(1-piperidinyl)-7,8,9,10-tetrahydro-1,2,4triazolo[3,4-a]phthalazine

An 11.20 gm (0.0500 mole) quantity of the compound of Example 7 was added to 50 ml of piperidine. The mixture was refluxed overnight, then evaporated, and the residue was triturated with water. The mixture was then stirred and the resulting solid was filtered off, washed with water and dried, yielding 12.15 gm of 3-amino-6-(1-piperidinyl)-7, 8,9,10-tetrahydro-1,2,4-triazolo[3,4-a]phthalazine; mp 230-232° C.

EXAMPLE 10

N-(7,8,9,10-Tetrahydro-6-(1-piperidinyl)-1,2,4-triazolo [3,4-a]phthalazin-3-yl)acetamide A 5.40 gm (0.020 mole) quantity of the compound of Example 9 was added to 3.1 gm (0.032 mole) of triethylamine and 380 mg of 4-dimethylaminopyridine. This mixture was added to 100 ml of $CH_2Cl_2$. To this mixture, 2.4 gm (0.031 mole) of acetyl chloride was added. The mixture was refluxed overnight and evaporated. The residue was triturated with ether, then filtered, yielding 4.14 gm of solid N-(7,8,9,10-tetrahydro-6-(piperidinyl)-1,2,4-triazolo [3,4-a]phthalazin-3-yl)acetamide; mp 214-216° C. (benzene-hexane). Calculated: C, 61.12; H, 7.05; N, 26.73. Found: C, 63.58; H, 7.76; N, 23.60.

EXAMPLE 11

N-(7,8,9,10-Tetrahydro-6-(1-piperidinyl)-1, 2,4-triazolo[3,4-a]phthalazin-3-yl)propanamide An 8.17 gm (0.030 mole) quantity of the compound of Example 9 was added to 3.54 gm (0.035 mole) of triethylamine, 300 mg of 4-dimethylaminopyridine, 3.24 gm (0.035 mole) of propionyl chloride and 50 ml of methylene chloride. This mixture was refluxed for 6½ hours. The solvent was evaporated. The residue was pationed between $CH_2Cl_2$ and water. The organic layer was washed with water, dried, and evaporated, resulting in a gummy residue. This residue was triturated with ether and hexane, producing a white solid. The solid was filtered and washed with ethane, then treated with benzene and hexane producing crystalline N-(7,8,9,10-tetrahydro-6-(1-piperidinyl)-1,2,4-triazolo [3,4-a]phthalazin-3yl)propanamide; mp 173-174° C. (benzene-hexane).

EXAMPLE 12

((7,8,9,10-Tetrahydro-6-(1-piperidinyl)-1,2,4-triazolo [3,4-a]phthalazin-3-yl)amino)oxoacetic acid methyl ester To 6.00 gm (0.022 mole) of the compound of Example 9 in $CH_2Cl_2$ was added 6.00 gm (0.0489 mole) of methyl oxalyl chloride. The reaction was slightly exothermic. The mixture was stirred for 30 minutes. A 2.7 gm quantity of additional acid chloride was added and the mixture was stirred for 4 hours, and then evaporated, leaving a gummy residue. The residue was partitioned between $CH_2Cl_2$ and water. The organic layer was dried and evaporated. The residue was triturated with ether leaving a white solid. The solid was filtered, washed with ether, and dried to give ((7,8,9,10-tetrahydro-6(1-piperidinyl)-1,2,4-triazolo [4,3-a]phthalazin-3yl-)amino)oxoacetic acid methyl ester which was recrystallized from toluene-hexane; mp 188° C. Calculated: C, 56.97; H, 6.19; N, 23.45. Found: C, 56.87; H, 6.24; N, 23.37.

EXAMPLE 13

((7,8,9,10-Tetrahydro-6-(1-piperidinyl)-1,2,4-triazolo [3,4-a]-phthalazin-3-yl)amino)oxoacetic acid ethyl ester A 6 00 gm (0.022 mole) quantity of the compound of Example 9 was taken up in methylene chloride. A 9.60 gm (0.07 mole) quantity of ethyl oxalyl chloride was added and the mixture was stirred at room temperature overnight. The mixture was partitioned between $CH_2Cl_2$ and water. The organic layer was dried and evaporated. The residue was triturated with ether to give ((7,8,9,10-tetrahydro-6-(1-piperidinyl)-1,2,4triazolo [3,4-a]phthalazin-3-yl)amino)oxoacetic acid ethyl ester which was recrystallized from toluene-hexane; mp 168-169° C. Calculated: C, 58.05; H, 6.50; N 22.57. Found: C, 58.06, H, 6.46; N, 22.71.

EXAMPLE 14

N-(7,8,9,10-Tetrahydro-6-(1-piperidinyl)-1,2,4-triazolo [3,4-a]phthalazin-3-yl)-N-(propanoyl)propanamide An 8.17 gm (0.030 mole) quantity of the compound of Example 9 was dissolved in 75 ml of dichloroethane, and 6.06 gm (0.060 mole) of triethylamine and 570 mg of 4-dimethylaminopyridine were added. A 6.0 gm (0.0648 mole) quantity of propionyl chloride was added and the resulting mixture was refluxed overnight. The mixture was then cooled and evaporated. The residue was partitioned between $CH_2Cl_2$/aq $NaHCO_3$. The organic layer was dried and evaporated, and triturated with ether-hexane, yielding 8.5 gm of N-(7,8,9,10-tetrahydro-6-(1-piperidinyl)-1,2,4-triazolo [3,4-a]phthalazin3-yl)-N-(propanoyl)propanamide which was recrystallized from toluene-hexane; mp 128-129° C.

EXAMPLE 15

3-Amino-6-(4-morpholinyl)-7,8,9,10-tetrahydro-1,2,4triazolo [3,4-a]phthalazine

A 22.40 gm (0.100 mole) quantity of 3-amino-6-chloro-7,8,9,10-tetrahydro-1,2,4-triazolo[3,4-a]phthalazine was added to 225 ml of morpholine and the mixture was refluxed for 7 hours. The mixture was then evaporated. A 250 ml volume of water was added to the residue and the mixture was stirred. The resulting solid was filtered and dried, yielding 27.2 gm of 3-amino-6-(4-morpholinyl)-7,8,9,10-tetrahydro-1,2,4triazolo [3,4-a]phthalazine; mp 260–262° C.

EXAMPLE 16

N-(7,8,9,10-Tetrahydro-6-(4-morpholinyl)-1,2,4-triazolo[3,4-a]phthalazin-3-yl)acetamide A 5.80 gm (0.0211 mole) quantity of the compound of Example 15 was dissolved in 100 ml of dichloroethane, and 380 mg (0.003 mole) of dimethylaminopyridine and 3.1 gm (0.03 mole) of triethylamine were added, followed by 2.38 gm (0.030 mole) of acetyl chloride. This mixture was refluxed overnight and evaporated. The resulting mixture was partioned between dilute aqueous NaHCO$_3$ and CH$_2$Cl$_2$. The organic layer was dried and evaporated. The residue was triturated with ether and the resulting solid was collected to give 4.40 g of N-(7,8,9,10-tetrahydro-6-(4-morpholinyl)-1, 2,4-triazolo[3,4-a]phthalazin-3yl)acetamide; mp 147–149° C. (toluene-hexane).

EXAMPLE 17

N-(7,8,9,10-Tetrahydro-6-(4-morpholinyl)-1,2,4-triazolo [3,4-a]phthalazin-3-yl)propanamide To a solution of 5.80 gm (0.0211 mole) of the compound of Example 15 in 50 ml of CH$_2$Cl$_2$ was added 3.03 g (0.03 mole) of triethylamine, 384 mg (0.003 mole) of 4-dimethylaminopyridine and 2.78 g (0.03 mole) of propionyl chloride. The mixture was heated at reflux for 15 hours, cooled, and partitioned between CH$_2$Cl$_2$ and aqueous NaHCO$_3$. The organic layer was dried (Na$_2$SO$_4$) and concentrated to give a thick oil which crystallized on trituration with toluene-hexane. The resulting white solid was collected to give 5.32 gm of N-(7,8,9,10-tetrahydro-6-(4-morpholinyl)-1,2,4-triazolo [3,4-a]phthalazin3-yl)propanamide; mp 164–166° C. (ethanol-ether). Calculated: C, 58.16; H, 6.71, N, 25.44. Found: C, 58.17; H, 6.70; N, 25.67.

EXAMPLE 18

((7,8,9,10-Tetrahydro-6-(4-morpholinyl)-1,2,4-triazolo [3,4-a]-phthalazin-3-yl)amino)oxoacetic acid ethyl ester A 5.80 gm (0.0211 mole) quantity of the compound of Example 15 was dissolved in 30 ml of CH$_2$Cl$_2$ and 4.09 gm (0.030 mole) of ethyl oxalyl chloride, 380 mg of 4-dimethylaminopyridine, and 3.09 gm (0.030 mole) of triethylamine were added. The mixture was heated on a steam bath for 4 hours. The mixture was then allowed to stand overnight at room temperature and evaporated. The residue was partitioned with CH$_2$Cl$_2$ and aqueous NaHCO$_3$. The organic layer was dried and evaporated. ((7,8,9,10-Tetrahydro-6-(4-morpholinyl)-1,2,4-triazolo [3,4-a]-phthalazin-3-yl)amino)oxoacetic acid ethyl ester was recrystalized from ether-isopropanol to give 4.58 gm of material, m.p. 148–150° C. Calculated: C, 54.53; H, 5.92; N, 22.45. Found: C, 54.25; H, 5.86; N, 22.85.

EXAMPLE 19

3-Amino-6-(4-morpholinyl)-7,8,9,10-tetrahydro-1,2,4triazolo [3,4-a]phthalazine hydrochloride Method A. A 1.00 gm (0.0036 mole) quantity of the compound of Example 15 was dissolved in 25 ml of ethanol and heated to boiling An ether solution of hydrogen chloride was added and the mixture was allowed to sit for 1 hour. Solid appeared and was washed with ether yielding 0.710 gm of 3-amino-6-(4-morpholinyl)-7,8,9,10-tetrahydro-1,2,4triazolo [3,4-a]phthalazine hydrochloride.

Method B. A 10.26 gm (0.0948 mole) quantity of the compound of Example 15 was dissolved in 350 ml of ethanol. The solution was cooled and saturated with HCl gas. The mixture was stirred for 30 minutes and allowed to stand for a few hours. The resulting solid was filtered off and washed with ether yielding 7.40 gm of 3-amino-6-(4-morpholinyl)-7,8,9,10-tetrahydro-1,2,4-triazolo [3,4a]phthalazine hydrochloride; mp 265–266° C. Calculated: C, 50.23; H, 6.16; N, 27.04. Found: C, 50.01; H, 6.15; N, 27.10.

EXAMPLE 20

N-(1-Oxopropyl)-N-(7,8,9,10-tetrahydro-6-(4-morpholinyl)-1,2,4triazolo [3,4-a]phthalazin-3-yl)propanamide If the product of Example 15 is reacted according to the procedure described in Example 18, the product obtained is N(1-oxopropyl)-N-(7,8,9,10-tetrahydro-6-(4-morpholinyl)-1,2,4- triazolo [3,4a]phthalazin-3-yl)propanamide.

EXAMPLE 21

3-Amino-6-(1-pyrrolidinyl)-7,8,9,10-tetrahydro-1,2,4triazolo [3,4-a]phthalazine

A 36.00 gm (0.161 mole) quantity of the compound of Example 7 was added to 125 ml of pyrrolidine and the mixture was refluxed for six hours. After cooling, the solid was filtered. The filtrate was evaporated, combined with the solid, and washed with water. The resulting solid was dried to yield 32.92 gm of 3-amino-6-(1-pyrrolidinyl)-7,8,9,10-tetrahydro-1,2,4-triazolo [3,4-a]phthalazine; mp 243–244° C. Calculated: C, 60.44, H, 7.02, N, 32.54. Found: C, 60.20, H, 7.06, N, 32.78.

EXAMPLE 22

((7,8,9,10-Tetrahydro-6-(1-pyrrolidinyl)-1,2,4-triazolo [3,4-a]phthalazin-3-yl)amino)oxoacetic acid ethyl ester To a solution of 7.00 gm (0.0271 mole) of the compound of Example 21 in 60 ml of CH$_2$Cl$_2$ was added 300 mg of 4-dimethylaminopyridine, 3.03 gm (0.03 mole) of triethylamine, and 4.30 gm (0.0315 mole) of ethyl oxalyl chloride. The resulting mixture was refluxed overnight and evaporated. The residue was partioned between CH$_2$C$_2$ and aqueous NaHCO$_3$. The organic layer was washed with water, dried, and evaporated. The residue was triturated with benzene and solid was collected to give 6.71 g of ((7,8,9,10-tetrahydro-6-(1-pyrrolidinyl)-1,2,4-triazolo [3,4a]phthalazin-3-yl)amino)oxoacetic acid ethyl ester; mp 195–197° C. (toluene-ethanol).

We claim:

1. A compound of the formula:

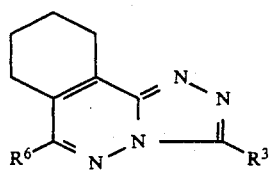

or the pharmaceutically acceptable acid addition salts thereof, wherein

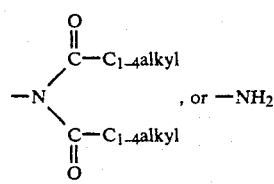

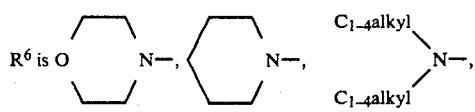

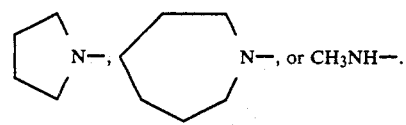

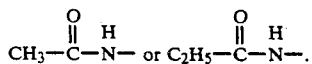

2. A compound according to claim 1 wherein $R^3$ is

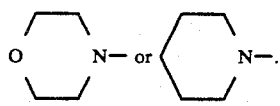

3. A compound according to claim 1 wherein $R^6$ is

4. A compound of claim 2 which is 3-amino-6-(methylamino)-7,8,9,10-tetrahydro-1,2,4-triazolo [3,4-a]phthalazine.

5. A compound of claim 2 which is 3-amino-6-(1-piperidinyl)-7,8,9,10-tetrahydro-1,2,4-triazolo [3,4-a]phthalazine.

6. A compound of claim 2 which is N-(7,8,9,10-tetrahydro-6-(1-piperidinyl)-1,2,4-triazolo [3,4-a]phthalazin-3-yl)acetamide.

7. A compound of claim 2 which is N-(7,8,9,10-tetrahydro-6-(1-piperidinyl)-1,2,4-triazolo [3,4-a]phthalazin-3-yl)propanamide.

8. A compound of claim 2 which is ((7,8,9,10-tetrahydro-6-(1-piperidinyl)imidazo[3,4-a]phthalazin-3-yl)amino)oxoacetic acid methyl ester.

9. A compound of claim 1 which is ((7,8,9,10-tetrahydro-6-(1-piperidinyl)pyrazolo[3,4-a]phthalazin-3-yl)amino)oxoacetic acid ethyl ester.

10. A compound of claim 1 which is N-(7,8,9,10-tetrahydro-6-(1-piperidinyl)-1,2,4-triazolo [3,4-a]phthalazin-3-yl)-N-(propanoyl)propanamide.

11. A compound of claim 1 which is 3-amino-6-(4-morpholinyl)-7,8,9,10-tetrahydro-1,2,4-triazolo [3,4-a]phthalazine.

12. A compound of claim 1 which is N-(7,8,9,10-tetrahydro-6-(4-morpholinyl)-1,2,4-triazolo [3,4-a]phthalazin-3-yl)acetamide.

13. A compound of claim 1 which is N-(7,8,9,10-tetrahydro-6-(4-morpholinyl)-1,2,4-triazolo [3,4-a]phthalazin-3yl)propanamide.

14. A compound of claim 1 which is N-(7,8,9,10-tetrahydro-6-(4-morpholinyl)-1,2,4-triazolo [3,4-a]phthalazin-3-yl)amino)oxoacetic acid ethyl ester.

15. A compound of claim 1 which is 3-amino-6-(4-morpholinyl)-7,8,9,10-tetrahydro-1,2,4-triazolo [3,4-a]phthalazine hydrochloride.

16. A compound of claim 1 which is N-((7,8,9,10-tetrahydro-6-(1-pyrrolidinyl)-1,2,4-triazolo [3,4-a]phthalazin3-yl)amino)oxoacetic acid ethyl ester.

17. A method of treating bronchial disorders which comprises the administration of a pharmaceutically effective bronchodilating amount of a compound of claim 1 to a patient in need thereof.

18. A method of treating allergic diseases, conditions, or reactions, which comprises the administration of a pharmaceutically effective antiallergenic amount of a compound of claim 1 to a patient in need thereof.

19. A pharmaceutical composition in unit dosage form comprising a pharmaceutical carrier and a compound according to claim 1.

* * * * *

UNITED STATES PATENT AND TRADEMARK OFFICE
CERTIFICATE OF CORRECTION

PATENT NO. : 5,011,835
DATED : April 30, 1991
INVENTOR(S) : Norton P. Peet and Shyam Sunder It is certified that error appears in the above-identified patent and that said Letters Patent is hereby corrected as shown below:

At Column 1, line 56, the patent reads "sec-butyl, sec-butyl," and should read -- sec-butyl, --.

At Column 7, line 64, the patent reads "(1piperidinyl)" and should read -- (1-piperidinyl) --.

At Column 10, line 27, the patent reads "6 00" and should read -- 6.00 --.

At Column 12, line 1, the patent reads "boiling An" and should read -- boiling. An --.

At Column 12, line 60, the patent reads "$CH_2C_2$" and should read -- $CH_2Cl_2$ --.

Signed and Sealed this

Thirteenth Day of October, 1992

*Attest:*

DOUGLAS B. COMER

*Attesting Officer*     Acting Commissioner of Patents and Trademarks